United States Patent
Haga et al.

(10) Patent No.: US 6,356,399 B1
(45) Date of Patent: Mar. 12, 2002

(54) LIGHT PROJECTING METHOD, SURFACE INSPECTION METHOD, AND APPARATUS USED TO IMPLEMENT THESE METHODS

(75) Inventors: Kazumi Haga; Motoshi Sakai; Zenta Ushiyama, all of Tokyo (JP)

(73) Assignee: NewCreation Co., Ltd., Tokyo (JP)

( * ) Notice: Subject to any disclaimer, the term of this patent is extended or adjusted under 35 U.S.C. 154(b) by 0 days.

(21) Appl. No.: 09/463,656

(22) PCT Filed: Jun. 18, 1998

(86) PCT No.: PCT/JP98/02694

§ 371 Date: May 5, 2000

§ 102(e) Date: May 5, 2000

(87) PCT Pub. No.: WO99/06868

PCT Pub. Date: Nov. 2, 1999

(30) Foreign Application Priority Data

Jul. 29, 1997 (JP) .............................................. 9-203353

(51) Int. Cl.$^7$ .......................... G02B 27/02; G01N 21/55
(52) U.S. Cl. ...................... 359/800; 359/642; 356/445; 356/600; 356/612; 356/237.2
(58) Field of Search ............................. 356/124, 124.5, 356/237.2–237.6, 601, 612, 445–448, 600; 359/642, 648, 662–664, 708, 718, 721, 738, 798–801

(56) References Cited

U.S. PATENT DOCUMENTS

| | | | |
|---|---|---|---|
| 3,484,150 A | 12/1969 | Taoka et al. ................ 359/227 |
| 3,815,998 A | * 6/1974 | Tietze ..................... 356/237.2 |
| 4,167,337 A | * 9/1979 | Jaerisch et al. ............. 356/354 |
| 4,547,073 A | * 10/1985 | Kugimiya .................. 356/371 |
| 4,657,396 A | * 4/1987 | Honda et al. ............... 356/394 |
| 5,497,234 A | 3/1996 | Haga ........................ 356/613 |
| 5,699,164 A | 12/1997 | Lehan et al. ................ 356/445 |
| 5,715,050 A | 2/1998 | Haga ...................... 356/237.1 |
| 5,737,074 A | 4/1998 | Haga et al. ................. 356/237 |
| 5,745,236 A | 4/1998 | Haga ........................ 356/600 |
| 5,894,353 A | * 4/1999 | Hotta et al. ................ 356/446 |

FOREIGN PATENT DOCUMENTS

| | | |
|---|---|---|
| EP | 0 800 076 | 10/1997 |
| JP | 42-9232 | 5/1967 |
| JP | 52-102772 | 8/1977 |
| JP | 54-30061 | 3/1979 |
| JP | 60-121412 | 6/1985 |
| JP | 61-273520 | 12/1986 |
| JP | 1-104507 | 4/1989 |
| JP | 4-107517 | 4/1992 |
| JP | 7-325036 | 12/1995 |
| JP | 6-317532 | 3/1996 |
| JP | 8-201304 | 8/1996 |
| JP | 10-31154 | 2/1998 |
| JP | 10-307011 | 11/1998 |

* cited by examiner

*Primary Examiner*—Georgia Epps
*Assistant Examiner*—Evelyn A. Lester
(74) *Attorney, Agent, or Firm*—Crowell & Moring LLP

(57) ABSTRACT

The present invention provides a light illuminating method, a surface examining method using the light illuminating method, and apparatuses for performing these methods. In the surface illuminating apparatus for illuminating an object with a light beam from a light source through a lens member for illumination, the lens member for illumination has a characteristics with respect to a longitudinal aberration caused by a spherical aberration in the light source side of the lens for illumination, that an amount of shift from a paraxial image surface to image formation points gradually increase or decrease, with an increase in height of light incidence into the lens; and the light source is set at a position in an outside of a group of the image formation points.

9 Claims, 9 Drawing Sheets

SPHERICAL ABERRATION
(LONGITUDINAL)

FIG. 5
(a)
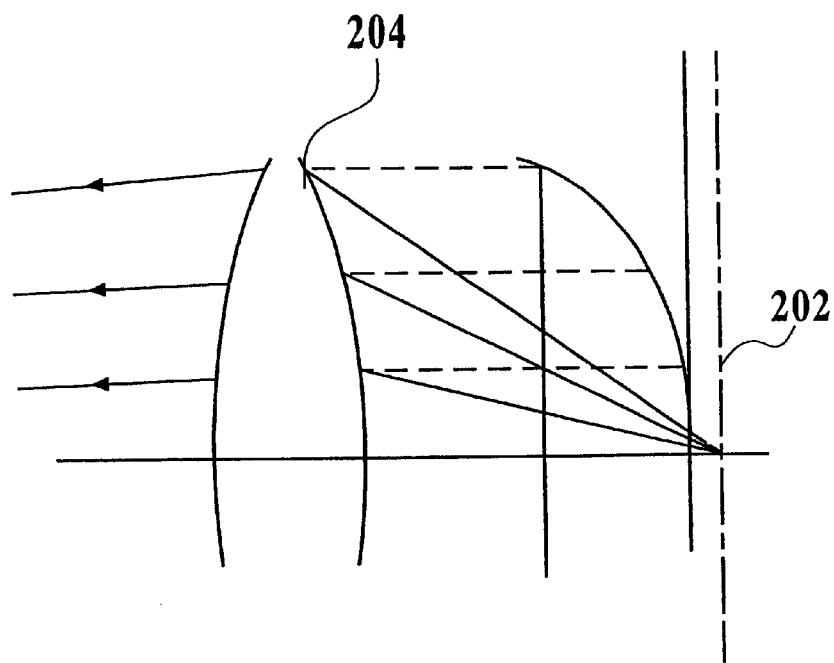
(b)
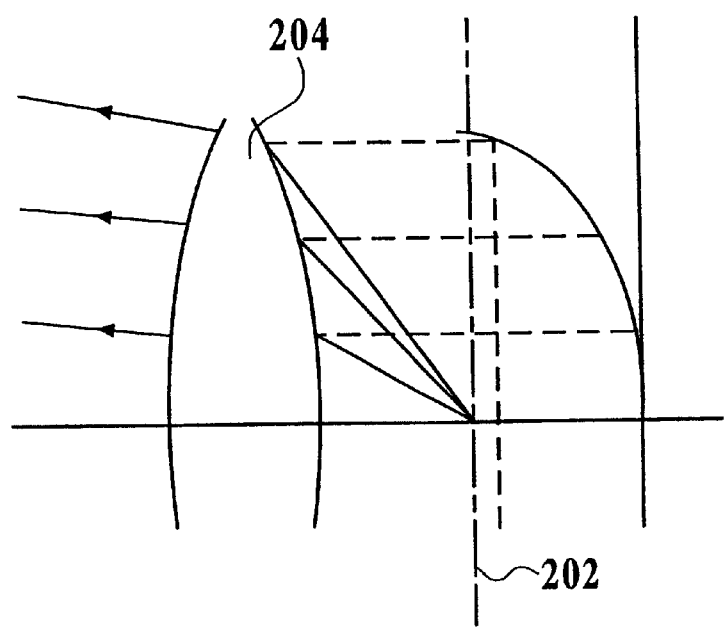

ILLUMINATION ANGULAR APERTURE
= OBJECT-SIDE ANGULAR APERTURE

ILLUMINATION ANGULAR APERTURE
= OBJECT-SIDE ANGULAR APERTURE

ILLUMINATION ANGULAR APERTURE = OBJECT-SIDE ANGULAR APERTURE

LIGHT PROJECTING METHOD, SURFACE INSPECTION METHOD, AND APPARATUS USED TO IMPLEMENT THESE METHODS

FIELD OF THE INVENTION

This invention relates to a light illuminating method, a surface examining method, and apparatuses for performing these methods.

BACKGROUND OF THE INVENTION

The applicant has already developed and filed an improved surface examining method and an improved apparatus for performing the method, as follows (U.S. Pat. No. 5,737,074).

The surface examining apparatus 10 comprises a light illuminating device 11 and an observation device 12, as shown in FIG. 12. The light illuminating device 11 comprises a light source 11a, an aperture stop 11b, a half mirror and a lens 11d for illumination. The light beam emitted out of the light source 11a is changed to a substantial point light source by the aperture stop 11b. The light beam from the point light source is reflected by the half mirror and is collimated through the lens 11d for illumination, to illuminate an object 13 to be measured. The observation device 12 comprises a lens system 12a for observation (the lens 11d for illumination also constitutes a part of the lens system 12a for observation), and an aperture stop 12b which is located at the position of a stop of the lens system 12a for observation. The light beam reflected by the object 13 to be measured forms an image on an image pickup part 14 through the observation lens system 12a and the aperture stop 12b. The observation lens system 12a and the aperture stop 12b constitutes an object-side telecentric optical system. In the specification, the meaning of the term "point light source" includes not only a light source which is considered to be a perfect point but also one having a size to a small degree.

In the surface examining apparatus 10, if it is assumed that the light source is considered to be a perfect point one (i.e., the illumination angular aperture is approximately 0°) and the object-side angular aperture of the aperture stop 12b is also approximately 0°, when observing the object 13 to be measured having an approximate flat surface without inclining, the image of the flat surface of the object 13 to be measured comes to have a luminance of 100% and the image of the slope of an irregularity of the object 13 comes to have a luminance of 0%.

On the other hand, if it is assumed that the light source is considered to be a substantial point one and has a predetermined illumination angular aperture and the object-side angular aperture of the aperture stop 12b is also approximately 0°, the image of the slope of the irregularity of the object 13 comes to have a luminance which depends on the angle of the slope.

When observing the object 13 to be measured by inclining itself, it is possible to obtain the image of the slope of the irregularity of the object 13 having a luminance which depends on the angle of the slope by optionally changing the luminance of the flat surface of the object 13, for example, to 0% or 50%.

Such an observation for the surface condition of the object 13 to be measured enables measurement of the presence or absence of irregularity and the condition of the irregularity on the basis of the luminance of the observed image.

However, as a result of observation for the surface condition of the object 13 to be measured, by using the above-described surface examining apparatus 10, the existence of white or black portions (missing portion) from which portions of image were missed was recognized in a relatively wide range. Existence of such missing portions makes hard to examine the entirety of the surface of the object 13 to be measured, accurately.

The present invention was developed in view of the above-described problems. An object of the present invention is to provide a light illuminating method which is suited for, e.g., observation for the surface condition of the object to be measured and the like, to provide a surface examining method using the light illuminating method, and to provide apparatuses for performing these methods.

DISCLOSURE OF THE INVENTION

Generally, a lens has a spherical aberration. In practice, because of the spherical aberration, as shown in FIG. 1, after the light beams entered a lens 1 in parallel to the optical axis thereof and passed through the lens 1, the light beams do not converge at a point. That is, the image formation points on the optical axis are shifted according to the heights of light beams entering the lens 1. This is the longitudinal aberration caused by a spherical aberration. A longitudinal aberration view in the case is shown in the right portion of the Figure.

When using a lens which has a longitudinal aberration for an observation device, generally, a plurality of lenses are combined so as to have an aberration curve of the so-called full correction, as shown in FIG. 2, and an image pickup surface is set at a position of the optimal image point in the inside of the group of image formation points on the optical axis.

In a light illuminating device, although the lens therefor has no aberration curve of full correction, generally, a point light source is set at a position of the optimal image point, like the case of an observation device, instead of an image pickup surface.

FIG. 3 shows an example of such a light illuminating device. The right side in this Figure is a longitudinal aberration view in the light source side. The lens (lens for illumination) 2 shown in this figure has a characteristic with respect to a longitudinal aberration caused by a spherical aberration in the light source side, that the amount of shift from the paraxial image surface gradually decreases with an increase in height of light incidence into the lens 2. In the light illuminating device, the point light source 3 is set at a position in the inside of the group of image formation points on the optical axis.

In the light illuminating device, by tracing back along the light beams after passing through the lens 2, from the side of the point light source 3, to study the change of inclination angle of the light beams with respect to the optical axis of the lens 2 in a direction perpendicular to the optical axis, it is understood that some points of inflection in the change of inclination angle of the lights, that is, points at which a plus sign or a minus sign of inclination of the lights is changed to the other, are created. When there is such a point of inflection in the change of inclination angle of the lights, the change of inclination angles of the lights reflected by an illuminated body (one having an approximately flat surface) comes also to have a point of inflection. In the case, the number of points of inflection in the change of inclination angle is the same as that of points of inflection in the change of reflection angle in a particular direction of the illuminated body.

When there are some points of inflection in the change of reflection angle of light beams in a particular direction of the illuminated body, an observation from a certain direction comes to give a noticeable unevenness of illumination. Therefore, existence of such a point of inflection is not preferable for a light illuminating device to which a uniform illumination on a surface to be illuminated is required. For a surface examining apparatus, unevenness of illumination on the surface to be illuminated leads to an inaccurate surface examination. Particularly, in a surface examining apparatus to observe the reflected light from an object to be measured through an aperture stop or an aperture, a phenomenon of partially missed image is often caused.

In such cases, when the number of points of inflection in the change of reflection angle in a particular direction of the illuminated body is one, it is possible to reduce unevenness of illumination or to optically cut the part of the image having unevenness of illumination, by changing the position of aperture in the light illuminating optical system or the observing optical system, or the like. However, when the number of points of inflection in the change of reflection angle in a particular direction of the illuminated body is two or more, it is difficult to reduce unevenness of illumination or to optically cut the part of the image having unevenness of illumination, by changing the position of aperture, or the like.

After consideration of these points, in order to make the change of reflection angle in a particular direction of the illuminated object to be measured, have only a point of inflection, the inventors have used a lens having a characteristics with respect to a longitudinal aberration caused by a spherical aberration in the light source side of the lens for illumination, that the amount of shift from the paraxial image surface to the image formation point gradually increases or decreases, with an increase in height of light incidence into the lens for illumination; and have set the point light source at a position in the outside of the group of image formation points on the optical axis. As a result of observation of the reflected light beams from the illuminated object to be measured, through an aperture stop or an aperture, it has been ascertained that no phenomenon of partially missed image is caused.

The present invention has been developed in view of the above-described knowledge. In accordance with an aspect of the present invention, the surface illuminating apparatus for illuminating with a light beam from a light source through a lens member for illumination, is characterized in that the lens member for illumination has a characteristics with respect to a longitudinal aberration caused by a spherical aberration in the light source side of the lens for illumination, that an amount of shift from a paraxial image surface to image formation points gradually increase with an increase in height of light incidence into the lens; and that the light source is set at a position in an outside of a group of the image formation points.

In accordance with another aspect of the present invention, the surface illuminating apparatus for illuminating with a light beam from a light source through a lens member for illumination, is characterized in that the lens member for illumination has a characteristics with respect to a longitudinal aberration caused by a spherical aberration in the light source side of the lens for illumination, that an amount of shift from a paraxial image surface to image formation points gradually decrease with an increase in height of light incidence into the lens; and that the light source is set at a position in an outside of a group of the image formation points.

The above-described phenomenon of partially missed image is also caused in the case of the point light source disposed out of the optical axis of the lens member for illumination or in the case of the light source being a surface illuminant (which corresponds to the case of point light sources disposed on and out of the optical axis). In the case, a comatic aberration introduces a problem. When the influence of the comatic aberration is not negligible, it is preferable that the lens member for illumination has a spherical aberration and a comatic aberration which have approximately the same shape as each other. The reason for this is that the spherical and comatic aberrations having approximately the same shape as each other enables easy determination of the optimal position of light source according to the spherical aberration view.

Preferably, a light beam from the light source is collimated through the lens member for illumination.

In accordance with another aspect of the present invention, the surface examining apparatus comprises the above-described surface illuminating apparatus and an observation device; wherein examination for a surface condition of an object to be measured is carried out by illuminating the surface of the object by the surface illuminating apparatus and by observing a reflected light beam from the object by the observation device.

The observation device preferably comprises an object-side telecentric optical system or an image-object-side telecentric optical system.

In accordance with another aspect of the present invention, the surface illuminating method for illuminating with a light beam from a light source through a lens member for illumination, comprises the steps of: preparing the lens member for illumination which has a characteristics with respect to a longitudinal aberration caused by a spherical aberration in the light source side of the lens for illumination, that an amount of shift from a paraxial image surface to image formation points gradually increase with an increase in height of light incidence into the lens; and setting the light source at a position in an outside of a group of the image formation points. The surface illuminating method for illuminating an object with a light beam from a light source through a lens member for illumination, may also comprises the steps of: preparing the lens member for illumination which has a characteristics with respect to a longitudinal aberration caused by a spherical aberration in the light source side of the lens for illumination, that an amount of shift from a paraxial image surface to image formation points gradually decrease with an increase in height of light incidence into the lens; and setting the light source at a position in an outside of a group of the image formation points.

In accordance with another aspect of the present invention, the surface examining method for examining a surface condition of an object to be measured, comprises the steps of; illuminating the surface of the object with a light beam by the method as described above, and observing a light beam reflected from the object.

According to the light illuminating method, the surface examining method using the light illuminating method, and the light illuminating device and the surface examining apparatus, for performing these methods, it is possible to make the created inflection point at which a plus sign or a minus sign of inclination of the light beams is changed to the other, only one, when tracing back along the light beams after passing through the lens for illumination, to study the change of inclination angle of the light beams with respect to the optical axis of the lens in a direction perpendicular to the optical axis. As the result, the method or apparatus according to the present invention enables reduction of unevenness of illumination to provide an ideal illumination, in comparison with the case having two or more inflection points. Use of the invention as a surface examining apparatus further enables reduction of phenomenon of partially missed image. In particular, it is possible to eliminate unevenness of illumination or to cut the part of the image having unevenness of illumination, by changing the position of aperture in the light illuminating optical system or the observing optical system.

BRIEF DESCRIPTION OF THE DRAWINGS

FIGS. 5(a) and 5(b) are views showing a set position of a point light source in the surface examining method and apparatus according to the present invention;

THE PREFERRED EMBODIMENT TO PERFORM THE INVENTION

Figure 1:
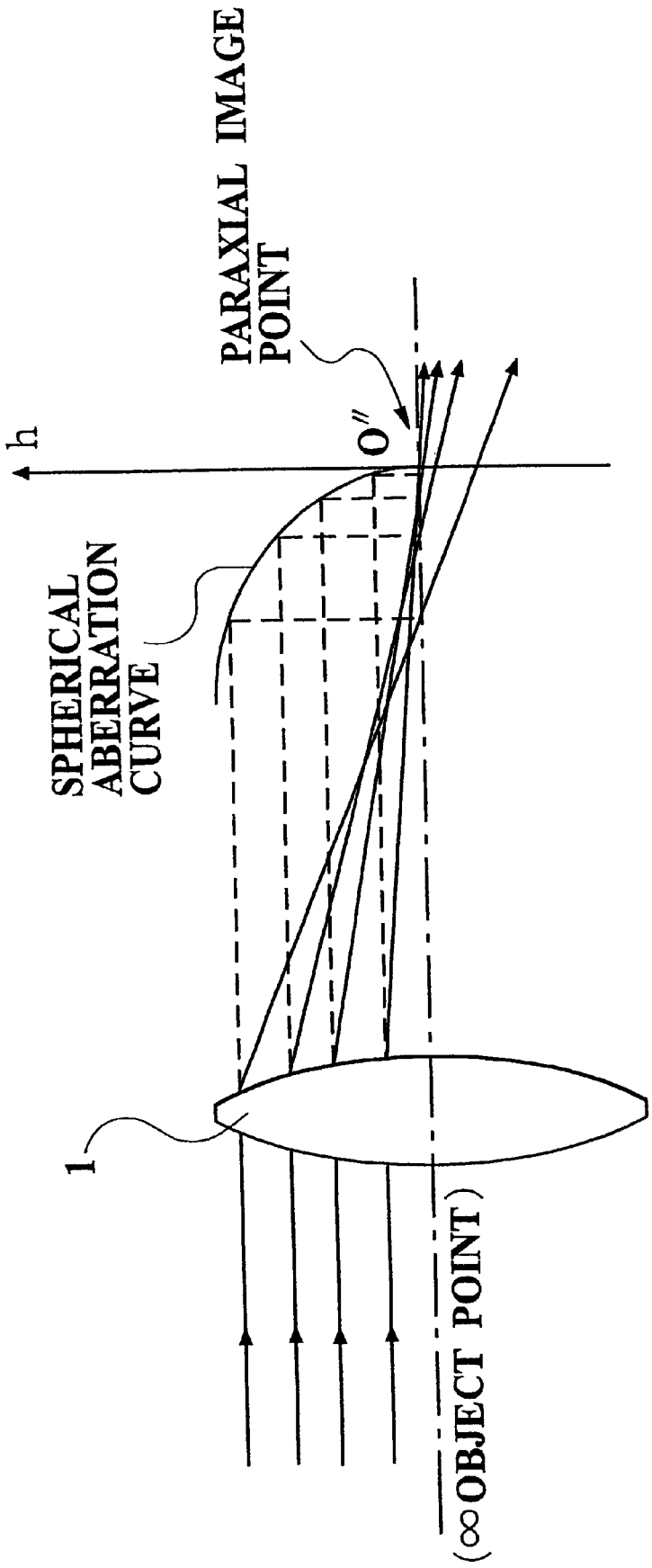
FIG. 1 is a view explaining a spherical aberration.
Figure 2:
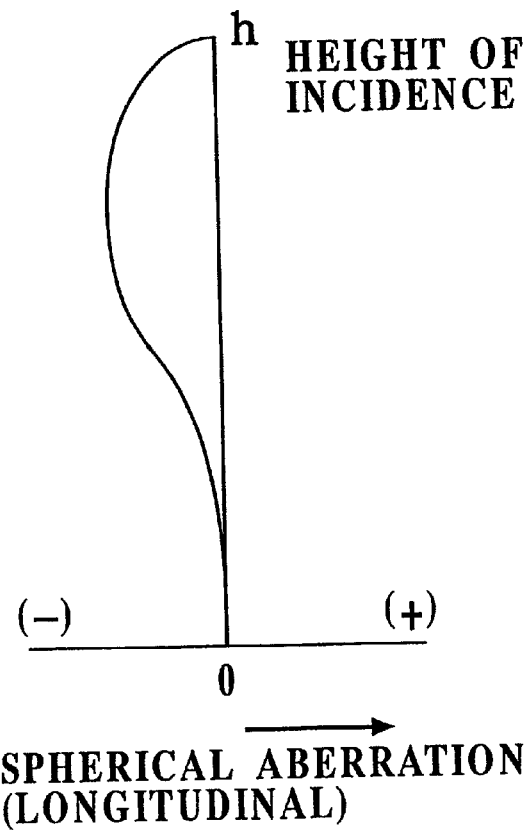
FIG. 2 is a view showing a spherical aberration having a shape of full correction.
Figure 3:
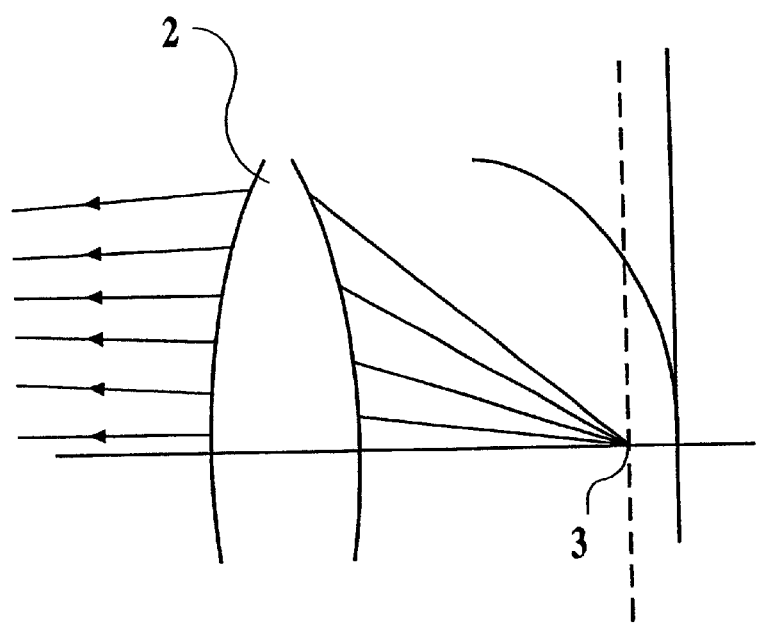
FIG. 3 is a view showing a set position of a point light source in a conventional method.
Figure 4:
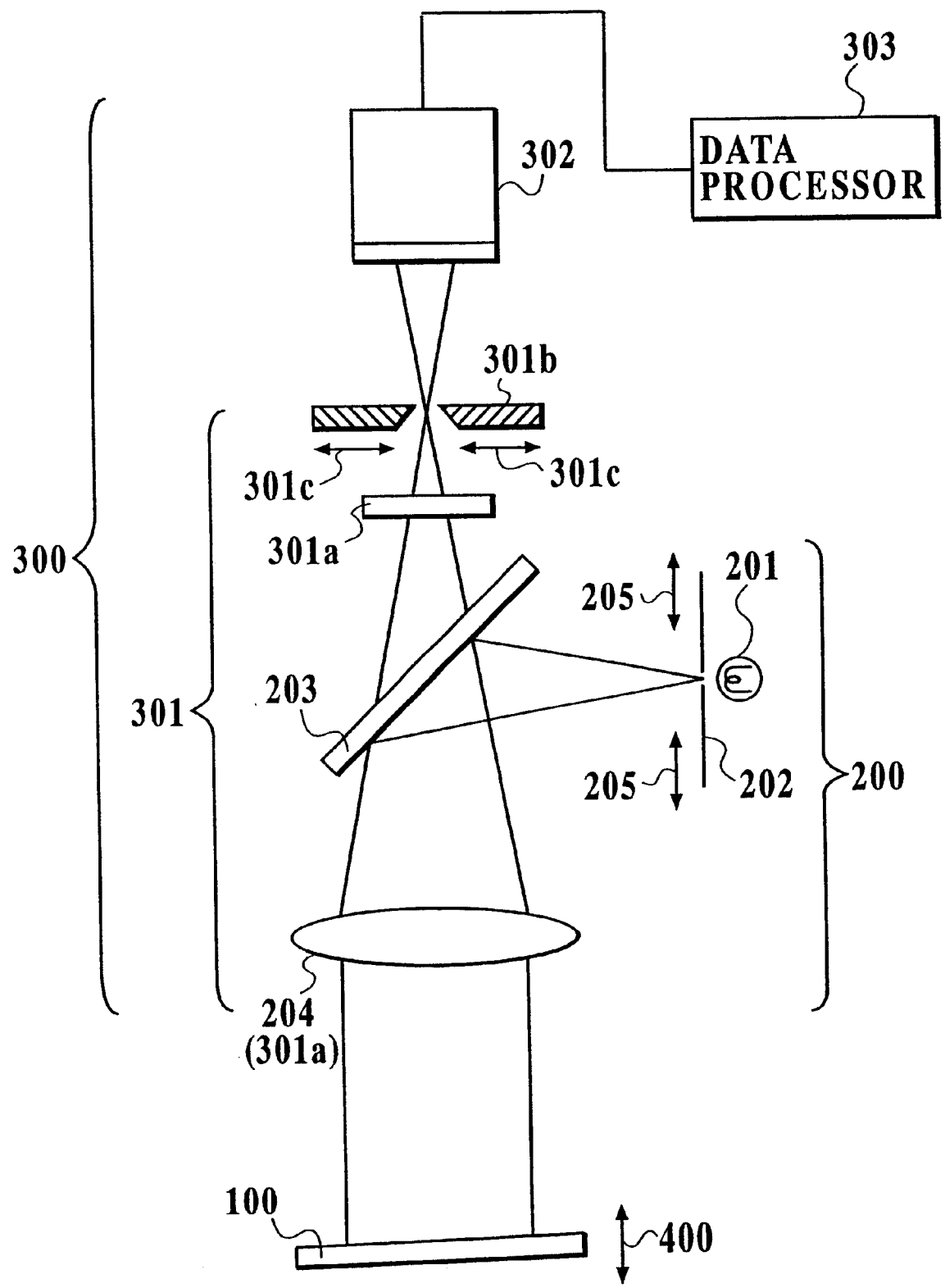
FIG. 4 is a view showing a construction of a surface examining apparatus according to the present invention.
Figure 6:
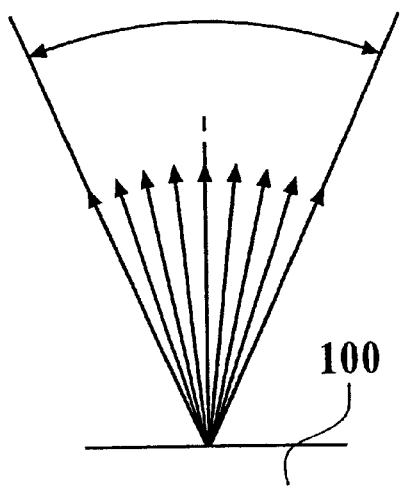
FIG. 6 is an explanation view of image forming operation of the surface examining method and apparatus according to the present invention.

In order to explain the present invention in detail, FIG. 4 shows the construction of the surface examining apparatus according to a first embodiment of the present invention. The surface examining apparatus is provided with a light illuminating device 200 for illuminating an object 100 to be measured with a light beam; and an observation device 300 for observing the light beam reflected from the object 100 to be measured. The surface examining apparatus is also provided with an angle setting member 400 which enables adjustment of an inclination angle of the object 100.

The light illuminating device 200 comprises a light source 201, an aperture stop 202, a half mirror 203 and a collimating lens (lens for illumination) 204. The aperture stop 202 is used for preparation of a point light source. The aperture diameter of the aperture stop 202 can be adjusted by an aperture changing member 205 and thus the illumination angular aperture to a point on the object 100 to be measured can be changed. In the case that adjustment of the angular aperture is not required, a light limiting member having a constant aperture diameter, e.g., an aperture or the like, may be used, instead of the aperture stop 202.

As the light source 201, although a light emitting element, a tungsten halogen lamp, a xenon lamp or the like may be used, it is not limited for this. For example, the light source may be provided with a surface illuminant which comprises a large number of glass fibers the outgoing ends of which are bound into a bundle, for introducing light beams from a light emitting element, a tungsten halogen lamp, a xenon lamp or the like, to select one or more from the large number of glass fibers to emit a light beam therefrom. Because such a light source enables making a point light source having a desired illumination angular aperture easily by selection of glass fibers, no aperture stop 202 is required.

The collimating lens 204 is for changing the light beam from the aperture stop 202 to a substantial parallel light beam. The collimating lens 204 in use has a characteristics with respect to a longitudinal aberration caused by a spherical aberration in the light source, that an amount of shift from a paraxial image surface to image formation points gradually decreases with an increase in height of light incidence into the collimating lens 204.

Set position of the aperture stop 202 is outside the group of the image formation points on the axis, in the case of consideration with respect to a longitudinal aberration caused by a spherical aberration in the light source. That is, when light beams in parallel with the optical axis (group of light beams having incidence heights different from one another) enter the collimating lens 204 from the side of the object 100 to be measured, the aperture stop 202 is set at a position on the axis outside the group of the image formation points formed by the group of light beams which passed through the collimating lens 204 and have incidence heights different from one another. The aperture stop 202 may be set in the side opposite to the bending direction of the longitudinal aberration curve with respect to the paraxial image surface, as shown in FIG. 5(a), and the aperture stop 202 may be set also in the same side as the bending direction of the longitudinal aberration curve with respect to the paraxial image surface, as shown in FIG. 5(b).

The observation device 300 comprises an object-side telecentric optical system 301 in which the average incident direction of light directing toward the object 100 to be measured coincides with the optical axis, an image pickup part 302 for picking up the light image formed by the object-side telecentric optical system 301, a data processing part 303 for processing the luminance data of the respective points on the object 100 to be measured, which are transmitted from the image pickup part 302, and a display (not shown) for displaying the surface condition of the object 100.

The object-side telecentric optical system 301 comprises an observation lens system 301a (in which the collimating lens 204 constitutes also a part of the observation lens system 301a) and an aperture stop 301b which is arranged at a position of a stop of the observation lens system 301a. The aperture diameter of the aperture stop 301b can be adjusted by an aperture changing member 301c and thus the illumination angular aperture to a point on the object 100 to be measured can be changed. In the case that adjustment of the angular aperture is not required, a light limiting member having a constant aperture diameter, e.g., an aperture or the like, may be used, instead of the aperture stop 301b.

The image pickup part 302 picks up the formed light image of the object 100 to be measured through the object-side telecentric optical system 301 and transmits the obtained luminance data thereof to the data processing part 303.

The data processing part 303 collects luminance data of respective points on the object 100 to be measured. Preferably, the luminance data are collected, for example, with 256 gradations.

The data processing part 303 performs finding an inclination distribution of the object 100 to be measured by first degree-differentiating the distribution of luminance data, finding the integrated data from the luminance data, finding a regression curve on the basis of the integrated data, and then finding the irregularity condition on the object 100 to be measured, by using the regression curve and the integrated data. The data processing part 303 detects various types of spatial frequency components by Fourier-transforming the luminance data of respective points on the object 100 for the predetermined direction on the object 100, or detects irregularity with a desired spatial frequency component by extracting predetermined frequency components from the spatial frequency components to compose them and by inverse Fourier-transforming the results. In order to perform Fourier transformation, although a fast Fourier transform device (FFT) can be preferably adopted, of course, because the object of the Fourier transformation is to perform spatial frequency separation, any device which enables spatial frequency separation of luminance data, other than an FFT, can also be used. For example, a discrete cosine transform device (DCT), a device which performs spatial frequency separation by the maximum entropy method, or the like can also be used.

The surface examining method or the apparatus therefor, of the embodiment can form an image of the reflected light issued from the object 100 to be measured with a luminance which depends on the inclination of the surface of respective points on the object 100 with respect to the reference plane, through the object-side telecentric optical system 301.

The reason for this will be explained as follows. In order to make a parallel luminous flux by a collimating lens 204, preparation of a point source is carried out by using a light source 201 and an aperture or aperture stop 202. However, because the aperture of the aperture stop 202 has a certain degree of size, a perfect point source cannot be obtained.

Accordingly, since the light beam collimated by the collimating lens 204 is not a perfect parallel beam, light beams having various angle components corresponding to the angular aperture of the aperture stop 202 are illuminated onto respective points on the object 100 to be measured. In other words, a point on the measurement object 100 is illuminated with an illuminating light having a certain illumination angular aperture. As a result, even when the measurement object 100 has an even surface, a divergent reflected light beam having a predetermined angle is generated at each point on the object 100.

Assuming now a case where the object-side angular aperture θ is set such that the whole reflected light beams from a surface parallel to a plane (a reference plane) perpendicular to the incident direction (an average incident direction) of the light enter just into the aperture stop 301b (that is, in the case of the illuminating angular aperture being equal to the object-side angular aperture θ), the incident light with a predetermined illuminating angular aperture is reflected on the object 100 to be measured, and the whole reflecting light are taken into the aperture of the aperture stop 301b to reach the image pickup part 302, so that a bright image with a luminance of 100% is obtained for the surface of this part.

Figure 7:
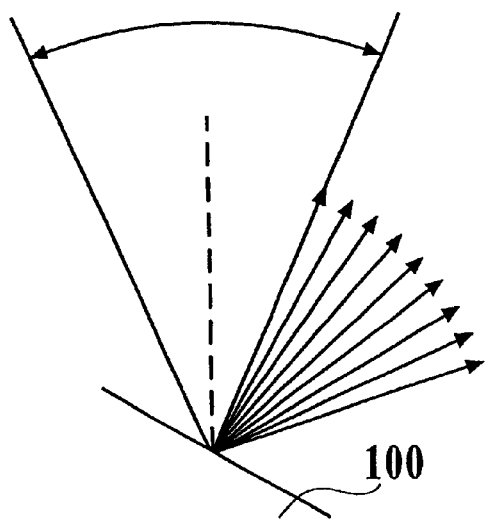
FIG. 7 is an explanation view of image forming operation of the surface examining method and apparatus according to the present invention.
Figure 8:
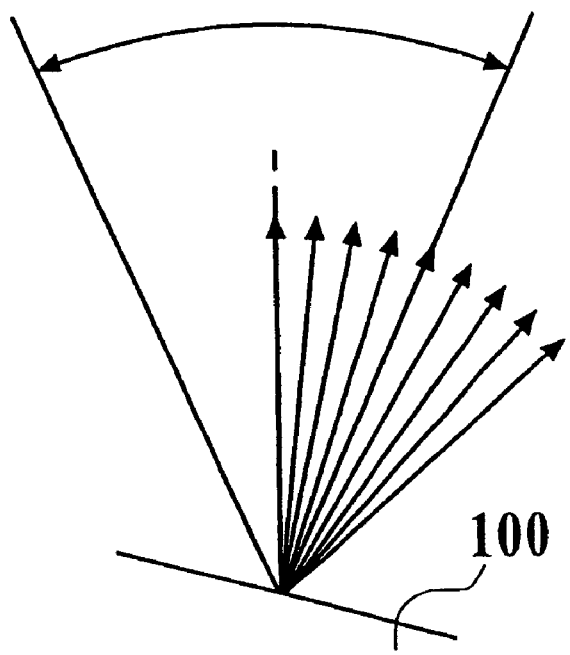
FIG. 8 is an explanation view of image forming operation of the surface examining method and apparatus according to the present invention.

On the other hand, in the case of the object 100 to be measured, inclined to the reference plane, the incident illuminating lights, as shown in FIGS. 7 and 8, are reflected on the surface of the object 100 to be measured, and the whole or a part of the reflected light are not taken into the aperture of the aperture stop 301b, so that the obtained image becomes a dark one with a luminance of 0% or one with a luminance corresponding to the quantity of light passing through the aperture of the aperture stop 301b.

Therefore, when it is assumed that a concave is found in the object (substantially flat surface) 100 to be measured and that there is a relationship between the inclination angle of the sloping surface of the concave=θ'/2, the diameter=L, and the depth=d, as shown in the following equation:

$$d=(L/2)\tan(\theta'/2),$$

the luminance at each point on the object 100 is as follows.

Figure 9:
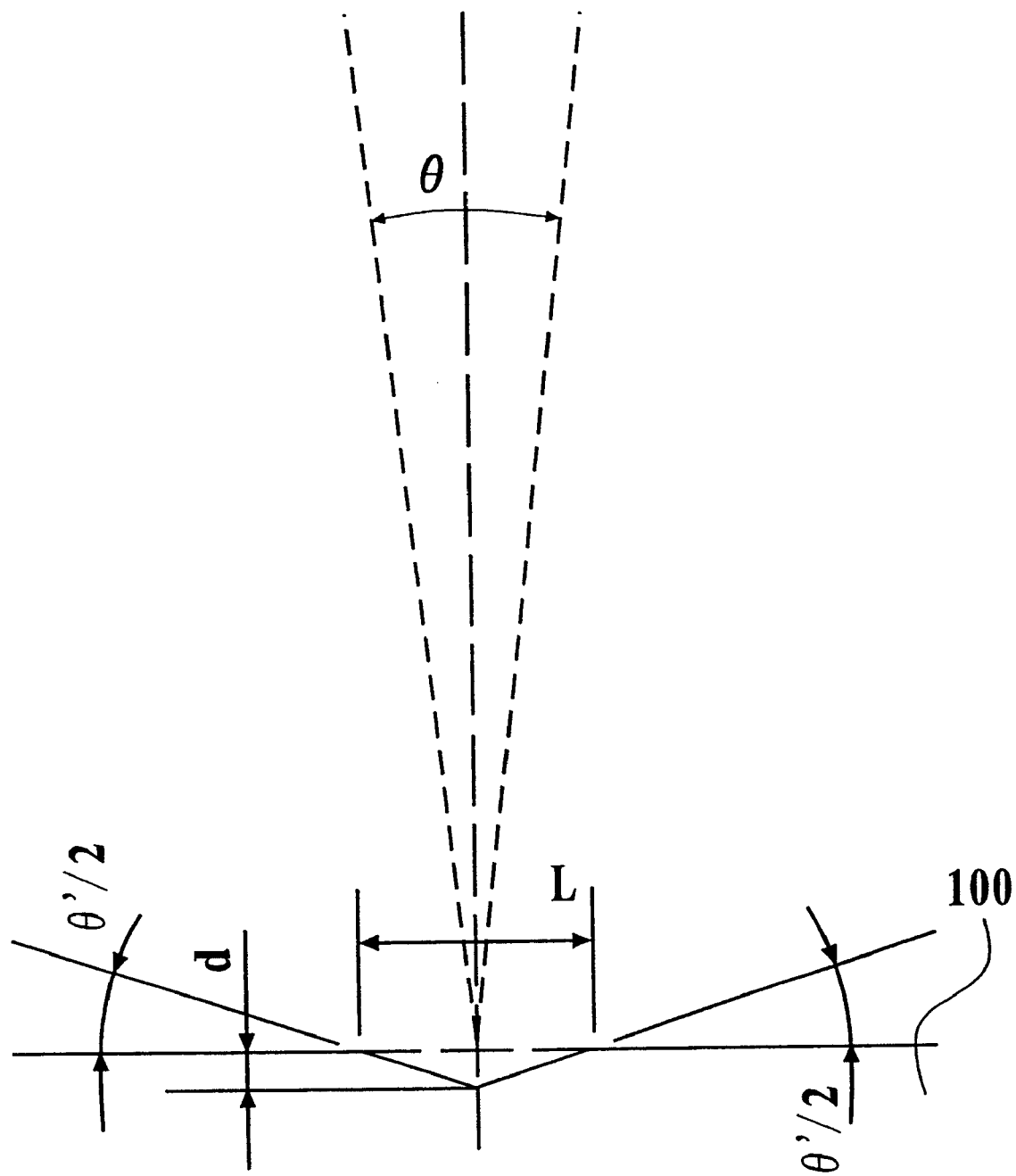
FIG. 9 is an explanation view of image forming operation of the surface examining method and apparatus according to the present invention.

In cases where the object-side angular aperture θ is set so that the whole reflected light beams from a surface parallel to the reference plane enter just the aperture of the aperture stop 301b, and the object 100 to be measured is illuminated with the illuminating light from the normal direction with respect to the object 100, when the inclination angle (θ'/2) of the slope of the concave is larger than (θ'/2), as shown in FIG. 9, the reflected light from the slope do not pass through the aperture of the aperture stop 301 at all, so that the obtained image of the concave has a luminance of 0%, while the image of the other portion (even surface portions) has a luminance of 100%. This condition is shown in FIG. 10.

When the measurement object 100 is inclined at an angle of θ" (=θ/4) from the state shown in FIG. 9, the inclination of one side slope (surface A) of the concave with respect to the reference plane is now ((θ'/2)−(θ/4)), and the inclination of the other side slope (surface B) with respect to the reference plane is ((θ'/2)+(θ/4)). In this case, when the inclination of the slope (θ'/2) is equal to (θ/4), because the one side slope (surface A) becomes parallel to the reference plane, the whole reflected light from the slope does enter the aperture of the aperture stop 301b. As a result, the image of the portion has a luminance of 100%. On the contrary, because the other side slope (surface B) has an inclination of (θ/2) with respect to the reference plane, the reflected light from the slope does not enter the aperture of the aperture stop 310 at all. Consequently, the image of the slope (surface B) has a luminance of 0%. In this case, because the even surface portion has an inclination of (θ/4) with respect to the reference plane, only a half of the reflected light from the even portion enter the aperture of the aperture stop 301b, the image of the even surface portion has a luminance of about 50%.

Figure 11:
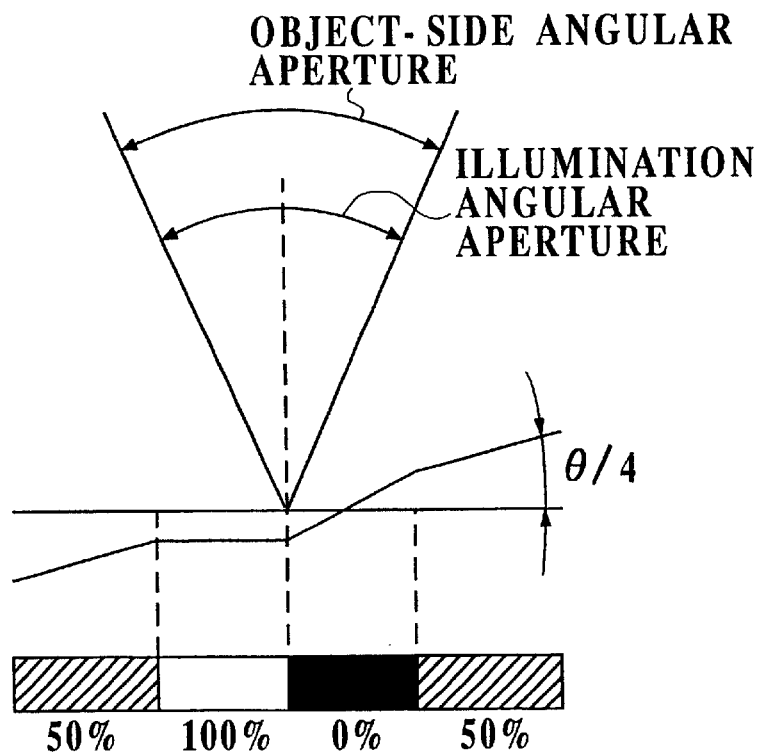
FIG. 11 is an explanation view of image forming operation of the surface examining method and apparatus according to the present invention.
Figure 12:
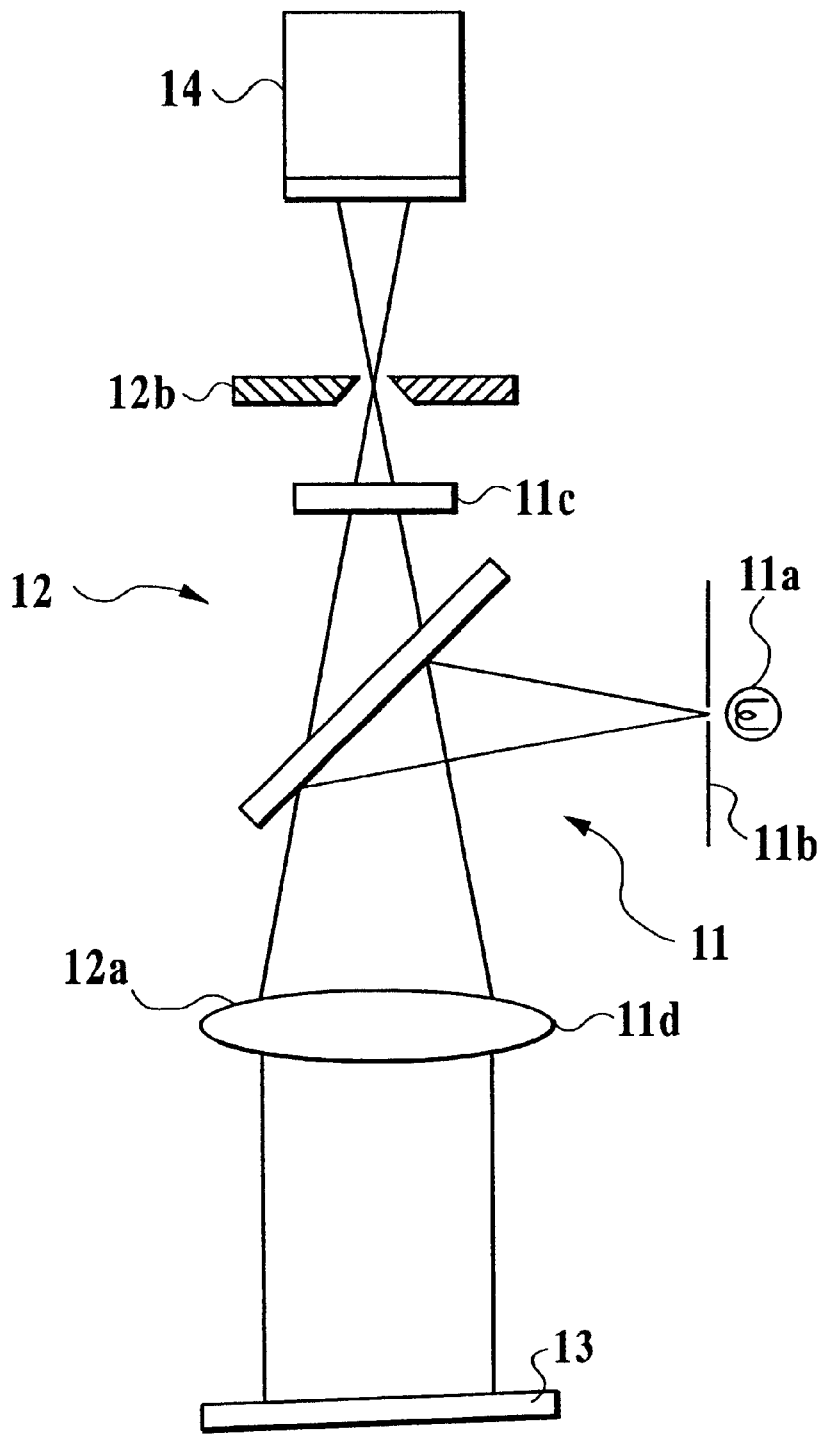
FIG. 12 is a view showing a construction of a conventional surface examining apparatus.

This condition is shown in FIG. 11.

Figure 10:
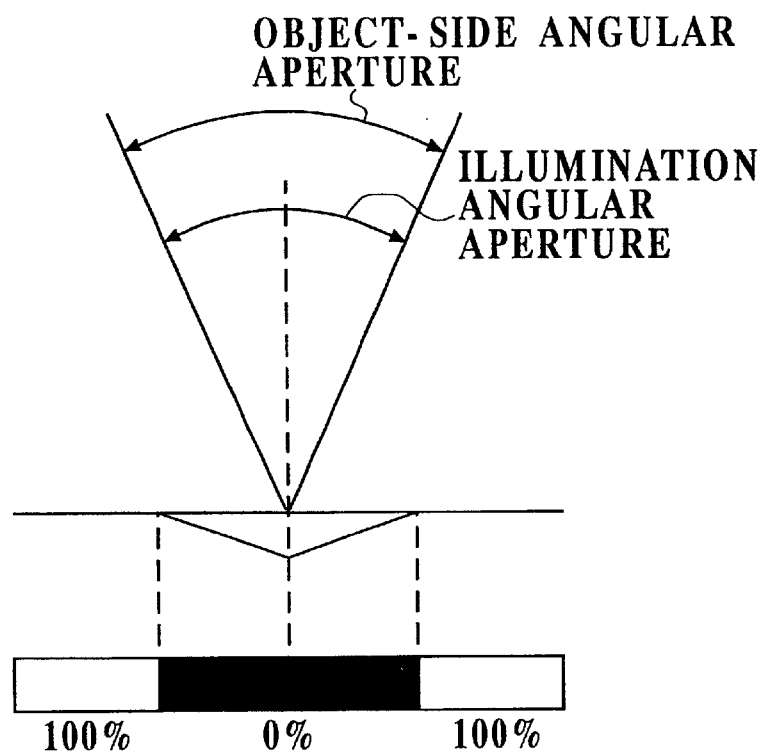
FIG. 10 is an explanation view of image forming operation of the surface examining method and apparatus according to the present invention.

On the other hand, in cases where the object-side angular aperture θ is set to be twice the divergent angle of the reflected lights at each portion on the even portion in the measurement object (in cases where twice the illuminating angular aperture is equal to the object-side angular aperture θ), when the measurement object is further inclined at an angle of θ" (=θ/4) with respect to the state shown in FIG. 10, the image of the even surface portion has a luminance of about 50%, the image of one slope (surface C) in the concave having an inclination angle (θ'/2) which is (θ/4) has a luminance of about 100%, and the image of the other slope (surface D) has a luminance of about 0%.

In the surface examining method or apparatus according to the above-described embodiments, an image is formed with a luminance corresponding to the incident angle at each point on the measurement object 100. It is possible to freely adjust the sensitivity for examining the concave by changing the divergent (spread) angle of the reflected light from the even portion in the measurement object 100, that is, the illuminating angular aperture, or by changing the object-side angular aperture θ.

Although only the surface examining method or apparatus according to the embodiments of the present invention has been explained, the present invention is not limited to such a surface examining method or apparatus according to the embodiments and various changes and modifications may be made thereto without departing from the gist thereof.

The surface illuminating apparatus according to the present invention is for illuminating with a light beam from a light source through a lens member for illumination, and is characterized in that the lens member for illumination has a characteristics with respect to a longitudinal aberration caused by a spherical aberration in the light source side of the lens for illumination, that an amount of shift from a paraxial image surface to image formation points gradually increase or decrease, with an increase in height of light incidence into the lens; and that the light source is set at a position in an outside of a group of the image formation points. The surface illuminating method according to the present invention is for illuminating with a light beam from a light source through a lens member for illumination, and comprises the steps of: preparing the lens member for illumination which has a characteristics with respect to a longitudinal aberration caused by a spherical aberration in the light source side of the lens for illumination, that an amount of shift from a paraxial image surface to image formation points gradually increase with an increase in height of light incidence into the lens, or the lens member for illumination which has a characteristics with respect to a longitudinal aberration caused by a spherical aberration in the light source side of the lens for illumination, that an amount of shift from a paraxial image surface to image formation points gradually decrease with an increase in height of light incidence into the lens; and setting the light source at a position in an outside of a group of the image formation points. Therefore, the surface illuminating apparatus or method according to the present invention enables reduction of unevenness of illumination to provide an ideal illumination.

The surface examining apparatus according to the present invention comprises the above-described surface illuminating apparatus and an observation device; wherein examination for a surface condition of an object to be measured is carried out by illuminating the surface of the object by the surface illuminating apparatus and by observing a reflected light beam from the object by the observation device. The surface examining method for examining a surface condition of an object to be measured, according to the present invention, comprises the steps of; illuminating the surface of the object with a light beam by the method as described above, and observing a light beam reflected from the object. Therefore, the method or apparatus according to the present invention enables reduction of unevenness of illumination in the region to be illuminated, and an accurate examination for the surface condition of the object to be measured.

The entire disclosure of Japanese Patent Application No. Tokugan hei-9-203353 filed on Jul. 29, 1997 including specification, claims, drawings and summary are incorporated herein by reference in its entirety.

INDUSTRIAL APPLICABILITY

As described above, the light illuminating method, a surface examining method using the light illuminating method, and apparatuses for performing these methods, according to the present invention are useful for illuminating an approximately flat surface with an extremely uniform light without unevenness of illumination and for examining the condition of a flat surface. For example, the invention may be used for examining the irregularity condition of the surface of a semiconductor wafer.

What is claimed is:

1. A surface illuminating apparatus for illuminating with a light beam from a light source through a lens member for illumination, characterized in that the lens member for illumination has a characteristics with respect to a longitudinal aberration caused by a spherical aberration in the light source side of the lens for illumination, that an amount of shift from a paraxial image surface to image formation points gradually increase with an increase in height of light incidence into the lens; and that the light source is set at a position in an outside of a group of the image formation points.

2. A surface illuminating apparatus for illuminating with a light beam from a light source through a lens member for illumination, characterized in that the lens member for illumination has a characteristics with respect to a longitudinal aberration caused by a spherical aberration in the light source side of the lens for illumination, that an amount of shift from a paraxial image surface to image formation points gradually decrease with an increase in height of light incidence into the lens; and that the light source is set at a position in an outside of a group of the image formation points.

3. A surface illuminating apparatus as claimed in claim 1, wherein the lens member for illumination has a spherical aberration and a comatic aberration, which have approximately the same shape as each other.

4. A surface illuminating apparatus as claimed in claim 1, wherein a light beam from the light source is collimated through the lens member.

5. A surface examining apparatus comprising a surface illuminating apparatus as claimed in claim 1, and an observation device; wherein examination for a surface condition of an object to be measured is carried out by illuminating the surface of the object by the surface illuminating apparatus and by observing a reflected light beam from the object by the observation device.

6. A surface examining apparatus as claimed in claim 5; wherein the observation device comprises an object-side telecentric optical system or an image-object-side telecentric optical system.

7. A surface illuminating method for illuminating with a light beam from a light source through a lens member for illumination, comprising the steps of:

preparing the lens member for illumination which has a characteristics with respect to a longitudinal aberration caused by a spherical aberration in the light source side of the lens for illumination, that an amount of shift from a paraxial image surface to image formation points gradually increase with an increase in height of light incidence into the lens; and setting the light source at a position in an outside of a group of the image formation points.

8. A surface illuminating method for illuminating with a light beam from a light source through a lens member for illumination, comprising the steps of:

preparing the lens member for illumination which has a characteristics with respect to a longitudinal aberration caused by a spherical aberration in the light source side of the lens for illumination, that an amount of shift from a paraxial image surface to image formation points gradually decrease with an increase in height of light incidence into the lens; and setting the light source at a position in an outside of a group of the image formation points.

9. A surface examining method for examining a surface condition of an object to be measured, comprising the steps of;

illuminating the surface of the object with a light beam by the method as claimed in claim 7, and observing a light beam reflected from the object.

* * * * *